United States Patent
Priore et al.

(10) Patent No.: US 9,157,800 B2
(45) Date of Patent: *Oct. 13, 2015

(54) SYSTEM AND METHOD FOR ASSESSING ANALYTES USING CONFORMAL FILTERS AND DUAL POLARIZATION

(71) Applicant: ChemImage Technologies LLC, Pittsburgh, PA (US)

(72) Inventors: Ryan Priore, Wexford, PA (US); Patrick Treado, Pittsburgh, PA (US); Matthew Nelson, Harrison City, PA (US)

(73) Assignee: ChemImage Technologies LLC, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/155,883

(22) Filed: Jan. 15, 2014

(65) Prior Publication Data

US 2014/0198315 A1 Jul. 17, 2014

Related U.S. Application Data

(60) Provisional application No. 61/752,817, filed on Jan. 15, 2013, provisional application No. 61/799,291, filed on Mar. 15, 2013.

(51) Int. Cl.
*G01J 4/00* (2006.01)
*G01J 3/32* (2006.01)
(Continued)

(52) U.S. Cl.
CPC ................. *G01J 3/32* (2013.01); *G01J 3/0224* (2013.01); *G01J 3/36* (2013.01); *G01J 3/457* (2013.01); *G01J 2003/1213* (2013.01); *G01N 21/31* (2013.01)

(58) Field of Classification Search
CPC ........... G01J 3/51; G01N 30/06; G01N 21/00; G01N 1/44; G01N 21/63
See application file for complete search history.

(56) References Cited

U.S. PATENT DOCUMENTS

| 4,749,257 A | 6/1988 | Klausz |
| 5,080,486 A | 1/1992 | Shirasaki |

(Continued)

FOREIGN PATENT DOCUMENTS

| AU | 2009354176 | 9/2010 |
| AU | 2009354176 | 1/2012 |

(Continued)

OTHER PUBLICATIONS

Onat, "A Solid-State Hyperspectral Imager for Real-Time Standoff Explosives Detection Using Shortwave Infrared Imaging.", 2009.

(Continued)

*Primary Examiner* — Tarifur Chowdhury
*Assistant Examiner* — Jamil Ahmed
(74) *Attorney, Agent, or Firm* — Pepper Hamilton LLP

(57) ABSTRACT

A system and method for detecting at least one target of interest using at least two conformal filters in a dual polarization configuration. A plurality of interacted photons are collected from a sample comprising at least one analyte of interest. The plurality of interacted photons are separated into at least a first and second optical component. The first optical component is passed through a first conformal filter and the second optical component is passed through a second conformal filter. A Data set corresponding to each filtered optical component is generated and an optical computation is applied to assess at least one characteristic of the analyte.

34 Claims, 11 Drawing Sheets

(51) Int. Cl.
  *G01J 3/36*   (2006.01)
  *G01J 3/457*  (2006.01)
  *G01J 3/02*   (2006.01)
  *G01J 3/12*       (2006.01)
  *G01N 21/31*      (2006.01)

(56) References Cited

U.S. PATENT DOCUMENTS

| | | |
|---|---|---|
| 5,097,352 A | 3/1992 | Takahashi |
| 5,321,539 A | 6/1994 | Hirabayashi |
| 5,657,121 A | 8/1997 | Nishina |
| 5,740,288 A | 4/1998 | Pan |
| 6,002,476 A | 12/1999 | Treado |
| 6,014,475 A | 1/2000 | Frisken |
| 6,198,531 B1 | 3/2001 | Myrick |
| 6,234,250 B1 | 5/2001 | Green |
| 6,262,851 B1 | 7/2001 | Marshall |
| 6,415,077 B1 | 7/2002 | Frisken |
| 6,522,467 B1 | 2/2003 | Li |
| 6,588,505 B2 | 7/2003 | Beck |
| 6,604,581 B2 | 8/2003 | Moake |
| 6,717,668 B2 | 4/2004 | Treado |
| 6,992,809 B1 | 1/2006 | Wang |
| 7,150,324 B2 | 12/2006 | Laursen |
| 7,336,323 B2 | 2/2008 | Wang |
| 7,362,489 B2 | 4/2008 | Wang |
| 7,411,786 B2 | 8/2008 | Wang |
| 7,460,227 B1 | 12/2008 | Kim |
| 7,623,233 B2 | 11/2009 | Freese |
| 7,697,141 B2 | 4/2010 | Jones |
| 7,848,000 B2 | 12/2010 | Wang |
| 7,859,753 B2 | 12/2010 | Wang |
| 7,911,605 B2 | 3/2011 | Myrick |
| 7,920,258 B2 | 4/2011 | Myrick |
| 8,027,855 B2 | 9/2011 | Freese |
| 8,049,881 B2 | 11/2011 | Myrick |
| 8,154,726 B2 | 4/2012 | Blackburn |
| 8,184,295 B2 | 5/2012 | Myrick |
| 8,208,147 B2 | 6/2012 | Myrick |
| 8,212,213 B2 | 7/2012 | Myrick |
| 8,213,006 B2 | 7/2012 | Myrick |
| 8,213,012 B2 | 7/2012 | Myrick |
| 8,237,920 B2 | 8/2012 | Jones |
| 8,237,929 B2 | 8/2012 | Myrick |
| 8,240,189 B2 | 8/2012 | Myrick |
| 8,283,633 B2 | 10/2012 | Myrick |
| 8,345,234 B2 | 1/2013 | Myrick |
| 8,352,205 B2 | 1/2013 | Myrick |
| 8,358,418 B2 | 1/2013 | Myrick |
| 8,379,199 B2 | 2/2013 | Myrick |
| 8,400,637 B2 | 3/2013 | Myrick |
| 8,406,859 B2 | 3/2013 | Zuzak |
| 2001/0013410 A1 | 8/2001 | Beck |
| 2001/0013411 A1 | 8/2001 | Beck |
| 2001/0042617 A1 | 11/2001 | Beck |
| 2001/0043146 A1 | 11/2001 | Beck |
| 2003/0108284 A1 | 6/2003 | Danagher |
| 2003/0192689 A1 | 10/2003 | Moake |
| 2004/0065475 A1 | 4/2004 | Laursen |
| 2004/0109232 A1 | 6/2004 | Riza |
| 2005/0015004 A1 | 1/2005 | Hertel |
| 2005/0148842 A1 | 7/2005 | Wang |
| 2005/0228452 A1 | 10/2005 | Mourias |
| 2006/0054780 A1 | 3/2006 | Garrood |
| 2006/0119797 A1 | 6/2006 | Ockenfuss |
| 2007/0294094 A1 | 12/2007 | Alessandrini |
| 2008/0212180 A1 | 9/2008 | Zhang |
| 2009/0002697 A1 | 1/2009 | Freese |
| 2010/0198080 A1 | 8/2010 | Liu |
| 2010/0225899 A1 | 9/2010 | Treado |
| 2010/0245096 A1 | 9/2010 | Jones |
| 2010/0285509 A1 | 10/2010 | Jones |
| 2011/0021908 A1 | 1/2011 | Lee |
| 2011/0104071 A1 | 5/2011 | Lee |
| 2011/0218736 A1 | 9/2011 | Pelletier |
| 2011/0271738 A1* | 11/2011 | McGill et al. ............... 73/23.41 |
| 2011/0279744 A1 | 11/2011 | Voigt |
| 2012/0018152 A1 | 1/2012 | Zuilekom |
| 2012/0062888 A1 | 3/2012 | Voigt |
| 2012/0150164 A1 | 6/2012 | Lee |
| 2012/0150451 A1 | 6/2012 | Skinner |
| 2012/0211650 A1 | 8/2012 | Jones |
| 2012/0268730 A1 | 10/2012 | Myrick |
| 2012/0279281 A1 | 11/2012 | Myrick |
| 2012/0300143 A1 | 11/2012 | Voigt |

FOREIGN PATENT DOCUMENTS

| | | |
|---|---|---|
| CA | 259621 | 8/2006 |
| CA | 2654783 | 3/2011 |
| CA | 2765477 | 4/2011 |
| GB | 2390423 | 1/2004 |
| WO | WO0118357 | 3/2001 |
| WO | WO0235059 | 5/2002 |
| WO | WO2004033841 | 4/2004 |
| WO | WO2006058306 | 6/2006 |
| WO | WO2006083720 | 8/2006 |
| WO | WO2006116031 | 11/2006 |
| WO | WO2007062201 | 5/2007 |
| WO | WO2007062202 | 5/2007 |
| WO | WO2007062224 | 5/2007 |
| WO | WO2007064575 | 6/2007 |
| WO | WO2007064578 | 6/2007 |
| WO | WO2007064579 | 6/2007 |
| WO | WO2008057905 | 5/2008 |
| WO | WO2008108846 | 9/2008 |
| WO | WO2008121715 | 10/2008 |
| WO | WO2010120285 | 10/2010 |
| WO | WO2011049571 | 4/2011 |
| WO | WO2011063086 | 5/2011 |
| WO | WO2012108685 | 8/2012 |
| WO | WO2012108886 | 8/2012 |
| WO | WO2012161694 | 11/2012 |
| WO | WO2012166138 | 12/2012 |

OTHER PUBLICATIONS

Kline, Nicole J. et al., "Raman Chemical Imaging of Breast Tissue," Journal of Raman Spectroscopy, vol. 28, 119-124 (1997).
Levenson, Richard, "Spectral Imaging and Pathology: Seeing More," Laboratory Medicine, Apr. 2004, vol. 35, [ages 244-251.
Levenson, Richard et al., "Multiplexing with Multispectral Imaging: From Mice to Microcopy," available from: http://www.cri-inc.com/assests/nuance/<ultiplexingwithMSIfrommicetomicroscopy.pdf, last accessed Nov. 23, 2010.
WO2006083720, International Search Report, Sep. 12, 2006.
WO2008057905, International Search Report, May 9, 2008.
WO2007064578, International Search Report, Mar. 25, 2008.
WO2001018357, International Search Report, Mar. 1, 2001.

* cited by examiner

300

310 — collecting a plurality of interacted photons from a sample, wherein the sample comprises at least one unknown material

320 — separating the plurality of interacted photons into at least a first optical component and a second optical component

330 — Passing the first optical component through at least one conformal filter, wherein each conformal filter comprises a tunable filter configured to filter an optical component conforming to at least one spectral shape associated with an analyte of interest

340 — passing the second optical component through at least one conformal filter

350 — generating a first data set corresponding to the first filtered optical component

360 — generating a second data set corresponding to the second filtered optical component

370 — applying at least one optical computation to the first data set and the second data set to assess the sample for at least one characteristic of the analyte

FIG. 3

SYSTEM AND METHOD FOR ASSESSING ANALYTES USING CONFORMAL FILTERS AND DUAL POLARIZATION

RELATED APPLICATIONS

This Application claims priority under 35 U.S.C. §119(e) to the following U.S. Provisional Patent Applications: No. 61/752,817, filed on Jan. 15, 2013, entitled "Pixilated Conformal Hyperspectral Imaging System and Method for Use Thereof," and No. 61/799,291, filed on Mar. 15, 2013, entitled "System and Method for Dual Polarization Using Conformal Filters." These applications are hereby incorporated by reference in their entireties.

BACKGROUND

Spectroscopic imaging combines digital imaging and optical spectroscopy techniques, which can include Raman scattering, fluorescence, photoluminescence, laser induced breakdown, ultraviolet, visible and infrared absorption spectroscopies. When applied to the chemical analysis of materials, spectroscopic imaging is also referred to as hyperspectral imaging or chemical imaging. Instruments for performing spectroscopic (i.e. chemical) imaging typically comprise an illumination source, image gathering optics, focal plane array (FPA) imaging detectors and imaging spectrometers.

In general, the size or accessibility of a sample determines the choice of image gathering optic. For example, a microscope is typically employed for the analysis of sub-micron to millimeter spatial dimension samples. For larger objects, in the range of millimeter to meter dimensions, macro lens optics are appropriate. For samples located within relatively inaccessible environments, flexible fiberscope or rigid borescopes can be employed. For very large scale objects, such as planetary objects, or for objects located at a significant stand-off distance from a sensor, telescopes are appropriate image gathering optics.

Two-dimensional, imaging FPA detectors are typically employed to detect images formed by the various optical systems. The choice of FPA detector is governed by the spectroscopic technique employed to characterize the sample of interest. For example, silicon (Si) charge-coupled device (CCD) detectors or complementary metal-oxide-semiconductor (CMOS) detectors are typically employed with visible wavelength fluorescence and Raman spectroscopic imaging systems, while indium gallium arsenide (InGaAs) FPA detectors are typically employed with near infrared spectroscopic imaging systems.

Conventional spectroscopic devices operate over a limited range of wavelengths due to the operation ranges of the detectors or imaging spectrometers possible. This enables analysis in the ultraviolet (UV), visible (VIS), near infrared (NIR), short wave infrared (SWIR), mid infrared (MIR), and long wave infrared (LWIR) wavelengths, as well as some overlapping ranges. These correspond to wavelengths of about 180-380 nm (UV), about 380-700 nm (VIS), about 700-2500 nm (NIR), about 850-1700 nm (SWIR), about 700-1700 (VIS-NIR), about 2500-5000 nm (MIR), and about 5000-25000 (LWIR).

Spectroscopic imaging of a sample is commonly implemented by one of two methods. First, point-source illumination can be used on a sample to measure the spectra at each point of the illuminated area. Second, spectra can be collected over the entire area encompassing a sample simultaneously using an electronically tunable optical imaging filter such as an acousto-optic tunable filter (AOTF), a liquid crystal tunable filter (LCTF), or a multi-conjugate tunable filter (MCF, which is a type of LCTF). Here, the organic material in such optical filters is actively aligned by applied voltages to produce the desired bandpass and transmission function. In hyperspectral imaging (HSI), the spectra obtained for each pixel of an image forms a complex data set referred to as a hyperspectral image. Hyperspectral images may contain the intensity values at numerous wavelengths or the wavelength dependence of each pixel element in the image. Multivariate routines, such as chemometric techniques, may be used to convert spectra to classifications.

A LCTF uses birefringent retarders to distribute the light energy of an input light signal over a range of polarization states. The polarization state of light emerging at the output of the LCTF is caused to vary as a function of wavelength due to differential retardation of orthogonal components of the light, contributed by the birefringent retarders. The LCTF discriminates for wavelength-specific polarization using a polarizing filter at the output. The polarizing filter passes the light components in the output that are rotationally aligned to the polarizing filter. The LCTF is tuned by adjusting the birefringence of the retarders so that a specific discrimination wavelength emerges in a plane polarized state, aligned to the output polarizing filter. Other wavelengths that emerge in other polarization states and/or alignments are attenuated.

A highly discriminating spectral filter is possible using a sequence of several birefringent retarders. The thicknesses, birefringences, and relative rotation angles of the retarders are chosen to correspond to the discrimination wavelength. More specifically, the input light signal to the filter becomes separated into orthogonal vector components, parallel to the respective ordinary and extraordinary axes of each birefringent retarder when encountered along the light transmission path through the filter. These separated vector components are differentially retarded due to the birefringence; such differential retardation also amounts to a change in their polarization state. For a plane polarized component at the input to the filter, having a specific rotational alignment at the input to the filter and at specific discrimination wavelengths, the light components that have been divided and subdivided all emerge from the filter in the same polarization state and alignment, namely plane polarized and in alignment with the selection polarizer (i.e., the polarizing filter) at the output.

A filter as described is sometimes termed a birefringent interference filter because the components that have been divided and subdivided from the input and interfere positively at the output selection polarizer are the components that are passed. Such filters also are sometimes described with respect to a rotational twist in the plane polarization alignment of the discriminated component between the input and the selection polarizer at the output.

There are several known configurations of spectral filters comprising birefringent retarders, such as the Lyot, Solc and Evans types. Such filters can be constructed with fixed (non-tunable) birefringent crystals for the retarders. A filter with retarders that are tuned in unison permits adjustment of the bandpass wavelength. Tunable retarders can comprise liquid crystals or composite retarder elements each comprising a fixed crystal and an optically aligned liquid crystal.

The thicknesses, birefringences, and rotation angles of the retarders are coordinated such that each retarder contributes part of the necessary change in polarization state to alter the polarization state of the passband wavelength from an input reference angle to an output reference angle. The input reference angle may be, for example, 45° to the ordinary and extraordinary axes of a first retarder in the filter. The output reference angle is the rotational alignment of the polarizing filter (or selection polarizer).

A spectral filter may have a comb-shaped transmission characteristic. Increasing or decreasing the birefringence when tuning to select the discrimination wavelength (or passband), stretches or compresses the comb shape of the transmission characteristic along the wavelength coordinate axis.

If the input light is randomly polarized, the portion that is spectrally filtered is limited to the vector components of the input wavelengths that are parallel to one of the two orthogonal polarization components that are present. Only light at the specific wavelength, and at a given reference polarization alignment at the input, can emerge with a polarization angle aligned to the rotational alignment of the selection polarizer at the output. The light energy that is orthogonal to the reference alignment at the input, including light at the passband wavelength, is substantially blocked.

A LCTF thus passes only one of two orthogonal components of input light. The transmission ratio in the passband is at a maximum for incident light at the input to the LCTF that is aligned to a reference angle of the LCTF. Transmission is at minimum for incident light energy at the input is orthogonal to that reference angle. If the input light in the passband is randomly polarized, the best possible transmission ratio in the passband is fifty percent. It is therefore desirable to devise a system and method wherein both orthogonal components of the input light are allowed to transmit through the tunable filter, thereby effectively doubling the throughput at the filter output.

Even using a dual polarization approach, each LCTF is limited to single bandpass, low throughput operation. Therefore, multiple, discrete bandpass measurements are required for analyte discrimination. The need for multiple measurements increases the overall measurement time.

Multivariate Optical Computing (MOC) is an approach which utilizes a compressive sensing device (e.g. an optical computer) to analyze spectroscopic data as it is collected. Other approaches utilize hard coated optical computing filters such as Multivariate Optical Elements (MOEs). MOEs are application-specific optical thin film filters that are used in transmission and reflectance modes. Thin film filters are interference filters with very thin structured layers of different materials with thicknesses on the order of the wavelengths of visible light (for example, 500 nm). Layers at this scale can have remarkable reflective properties due to the light wave interference and the difference in refractive index between the layers, the air, and the substrate. These effects alter the way the optic reflects and transmits light, an effect known as thin film interference. In manufacturing, thin film layers can be achieved through the deposition of one or more thin layers of material onto a substrate. This can be done using a physical vapor deposition process, such as evaporation or sputter deposition, or a chemical process such as chemical vapor deposition. The radiometric response of a MOE-based instrument is proportional to the intended analyte in an associated matrix.

Compressive sensing is the process in which a fully resolved waveform or image is reconstructed from a small set of sparse measurements. A sparse sample implies a waveform or image data set with coefficients close to or equal to zero. Compressive sensing utilizes the redundancy in information across the sampled signal similar to lossy compression algorithms utilized for digital data storage. A fully expanded data set may be created through the solution of an undetermined linear system, an equation where the compressive measurements collected are smaller than the size of the original waveform or image. Compressive measurements can ultimately lead to expedited HSI data collections while still preserving most of the original spectroscopic and spatial information.

While compressive sensing holds potential for decreasing measurement time, the use of MOEs have limitations. For example, MOEs are fixed and lack flexibility for adapting to different analytes. There exists a need for an adaptable filter that can be used to detect a wide variety of analytes while reducing overall measurement time. It would be beneficial if a plurality of such filters could be arranged in a dual polarization configuration to further increase speed of analysis and also provide for assessing multiple analytes simultaneously.

SUMMARY

The system and method of the present disclosure overcome the limitations of the prior art by providing a flexible, adaptable filter that can be configured to assess a wide variety of different analytes. A conformal filter is an adaptable filter with the flexibility of conforming to a specific, broadband spectral feature (e.g. pattern or shape). A conformal filter simultaneously transmits multiple passbands that improve discrimination performance for analytes (e.g., discriminating between a target analyte and background), by increasing the throughput of a tunable filter and by increasing the speed of analysis. Conformal filters based on LCTF technology provide an electro-optical filter, with no mechanical moving parts, that collects all wavelengths of light simultaneously, making it unnecessary to continuously tune. Therefore, they can be rapidly tuned with automatable random accessing under computer control. There is no need for iterative tuning to capture all measurements (all wavelengths). The system of the present disclosure holds potential for dramatically improving the speed, performance, and agility of liquid crystal based HSI systems.

Each configuration of a conformal filter is designed to filter interacted photons conforming to at least one spectral shape associated with an analyte of interest. The conformal filter may be configured to operate in conjunction with at least one look-up table (LUT), providing flexibility for detecting multiple analytes of interest in near real-time. The LUT may comprise at least one voltage associated with each stage of the tunable filter. Each voltage is configured to cause the tunable filter to conform to a spectral shape associated with the analyte when applied to the associated stage.

The spectral shape of the conformal filter may be visualized as a traditional multivariate regression vector (e.g. Partial Least Squares—PLS) but is not limited to this in practice. The optical computation occurs by convolving the transmission profile of the conformal filter with the incident radiation from the target and summing the result onto a broadband optical imaging detector. Conformal filter HSI realizes both a Jacquinot and multiplexing advantage over traditional dispersive spectroscopy and discrete bandpass HSI in addition to a potential order of magnitude decrease in measurement time. It is this encoded, multivariate spectral pattern that provides the conformal filter HSI superior specificity over the conventional operation mode of rapidly tuning through a subset of discrete bands.

The present disclosure provides for a system comprising a first optical element, configured to separate a plurality of interacted photons generated from a sample into at least a first optical component and a second optical component. The system may comprise at least one conformal filter assembly, wherein each conformal filter assembly is configured to filter the first optical component and the second optical component conforming to at least one spectral shape associated with an analyte of interest. Each conformal filter assembly may comprise a first conformal filter configured to filter the first optical component and a second optical component configured to filter the second optical component. At least one detector may be configured to detect at least one of the first filtered optical component and the second filtered optical component and generate at least one of a first data set and a second data set.

The present disclosure also provides for a method for assessing characteristics of analytes in a sample. The method may comprise collecting a plurality of interacted photons from a sample and separating the plurality of interacted photons into at least a first optical component and a second optical component. The first optical component and second optical component may each be passed through at least one conformal filter. Each conformal filter may comprise a tunable filter configured to filter an optical component conforming to at least one spectral shape associated with an analyte of interest. A first data set and a second data set may be generated corresponding to the first optical component and the second optical component. At least one optical computation may be applied to at least one of the first data set and the second data set to assess the sample for at least one characteristic of the analyte.

The present disclosure also provides for a system comprising a processor and a non-transitory processor-readable storage medium in operable communication with the processor, wherein the storage medium contains one or more programming instructions that, when executed, cause the processor to perform the following: collect a plurality of interacted photons from a sample, separate the plurality of interacted photons into at least a first optical component and a second optical component, pass the first optical component through at least one conformal filter, pass the second optical component through at least one conformal filter, generate a first data set corresponding to the first filtered optical component, generate a second data set corresponding to the second filtered optical component, and apply at least one optical computation to the first data set and the second data set to assess the sample for at least one characteristic of an analyte.

A system of the present disclosure may comprise a pixilated conformal filter (PCF). The PCF approach takes the light reflected, scattered, transmitted, and/or emitted from a surface of interest and using a lens array, distributes the reflected image over a plurality of conformal filter assemblies. Using another lens array, the system may focus the filtered images onto one or more detectors, such as FPAs, for capture. The two-dimensional FPAs provide spatial information associated with the sample. Each pair of images produced represents a positive and negative portion of a regression vector that may be processed mathematically. Each conformal filter pair may represent an analyte of interest. Because of the inherent polarized operation of liquid crystal filters, additional "pixels" can be obtained without further complicating the primary lens array by employing a polarization beamsplitter after the primary array and orienting the polarization axes of the LC conformal filters to split polarizations. This configuration holds potential for assessing a plurality of analytes simultaneously.

BRIEF DESCRIPTION OF THE DRAWINGS

The accompanying drawings, which are included to provide further understanding of the disclosure and are incorporated in and constitute a part of this specification illustrate embodiments of the disclosure, and together with the description, serve to explain the principles of the disclosure.

In the Drawings:

FIG. 1A is illustrative of a conformal filter embodiment. FIG. 1B is illustrative of a conformal filter embodiment comprising a rotatable aperture. FIG. 1C is illustrative of a conformal filter embodiment comprising a MCF design.

FIG. 3 is illustrative of a method of the present disclosure.

FIG. 5A illustrates an exemplary experimental set up comprising ammonium Nitrate (AN), ammonium sulfate (AS), and urea samples. FIG. 5B illustrates imaging results using a method of the present disclosure. FIG. 5C illustrates detection performance for discriminating between AN and AS.

DETAILED DESCRIPTION

Reference will now be made in detail to the embodiments of the present disclosure, examples of which are illustrated in the accompanying drawings. Wherever possible, the same reference numbers will be used throughout the specification to refer to the same or like parts.

The present disclosure provides for a system and method for assessing characteristics of analytes in a sample using conformal filters. In one embodiment, the conformal filters may comprise tunable filters, such as LCTFs. LCTFs are optical filters that use electronically-controlled liquid crystal elements to transmit a selectable wavelength, or plurality of wavelengths, and exclude others. Often, the basic working principle of LCTFs is based on the Lyot filter which consists of fixed retardance birefringence elements, fixed wave plates, and polarizers. A key difference between a Lyot filter and a LCTF is that the fixed wave plates are replaced by tunable liquid crystal wave plates in the LCTF. Designs other than the Lyot design may also be used. Examples of tunable filters that may be configured for use as a conformal filter may include at least one of: a LCTF, an AOTF, a Lyot LCTF, an Evans Split-Element LCTF, a Solc LCTF, a Ferroelectric LCTF, and a Fabry Perot LCTF.

In one embodiment, the tunable filter may comprise a MCF. A MCF is an imaging filter with serial stages along an optical signal path in a Solc filter configuration. Angularly distributed retarder elements of equal birefringence are stacked in each stage, with a polarizer between stages. The retarders can include tunable (such as abutted liquid crystals tuned in unison), fixed and/or combined tunable and fixed birefringences. In one embodiment, quartz retarders may be used. Although the retardations are equal within each stage, distinctly different retardations may be used for two or more different stages. This causes some stages to pass narrow bandpass peaks and other stages to have widely spaced bandpass peaks. The transmission functions of the serial stages are superimposed with selected tunable peaks coinciding. The resulting conjugate filter has a high finesse ratio and good out of band rejection. In one embodiment, the MCF may comprise filter technology available from ChemImage Corporation, Pittsburgh, Pa.

Figure 1A:
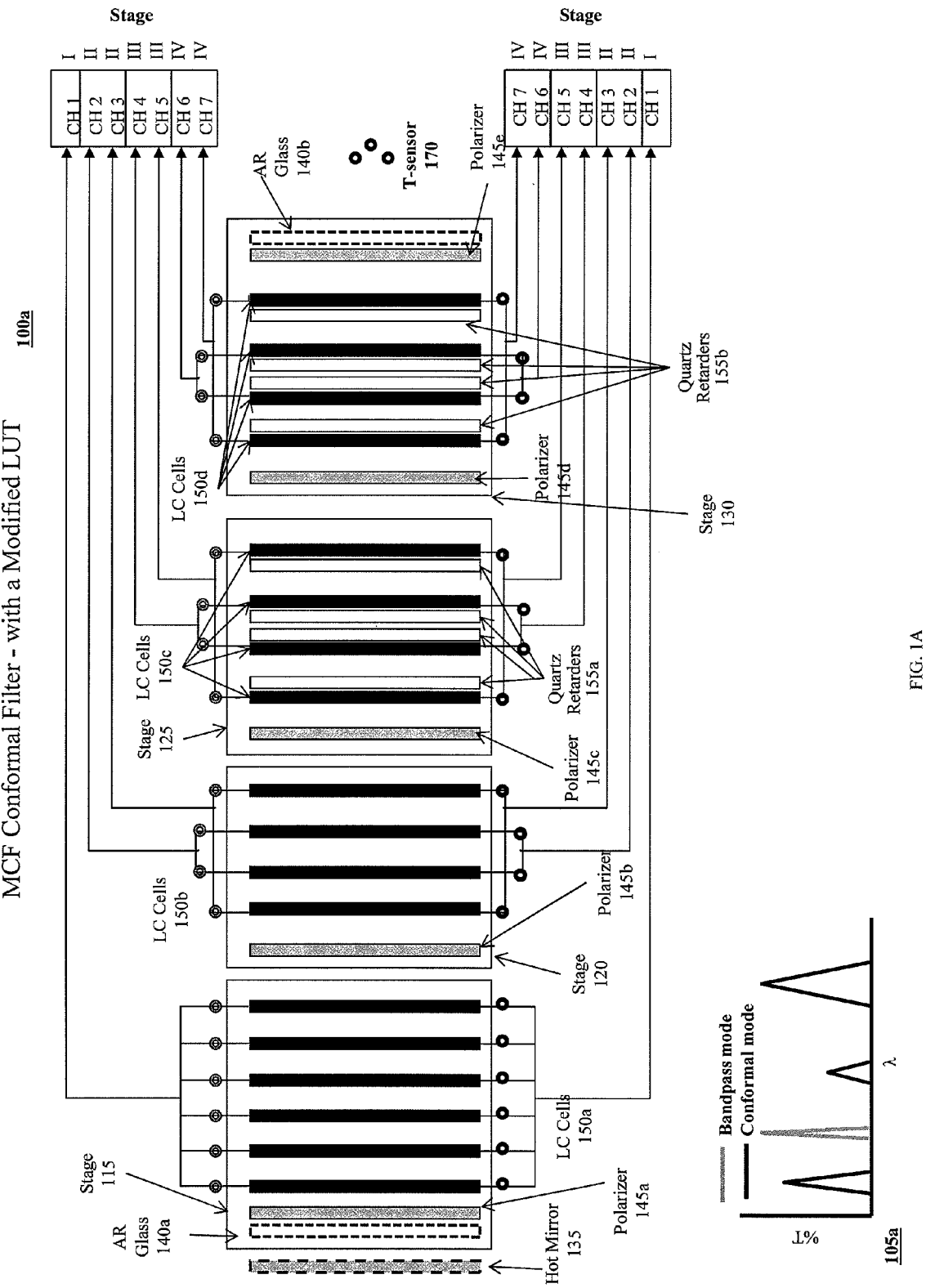
FIGS. 1A-1C are illustrative of exemplary conformal filter embodiments of the present disclosure.
Figure 1B:
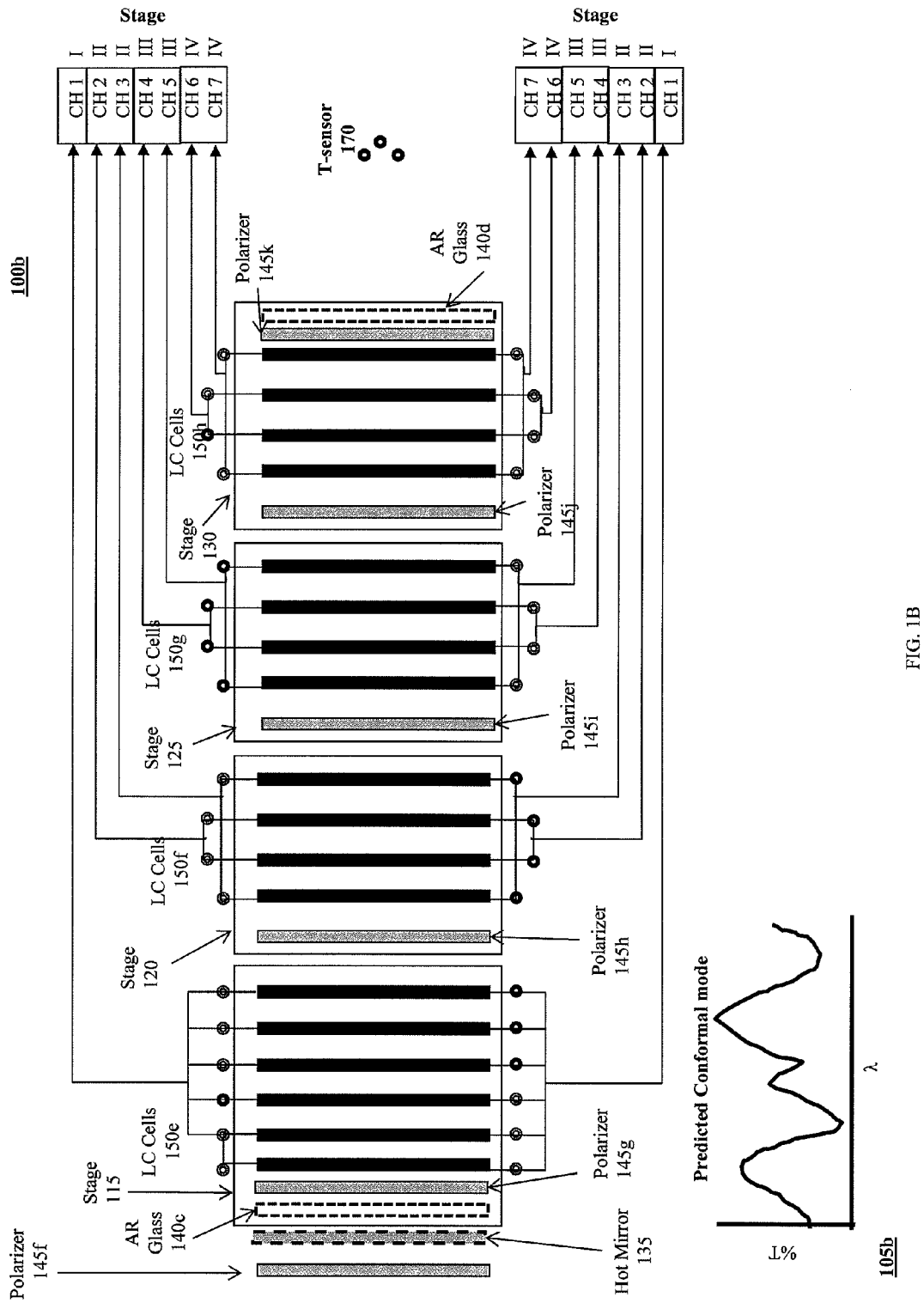
Figure 1C:
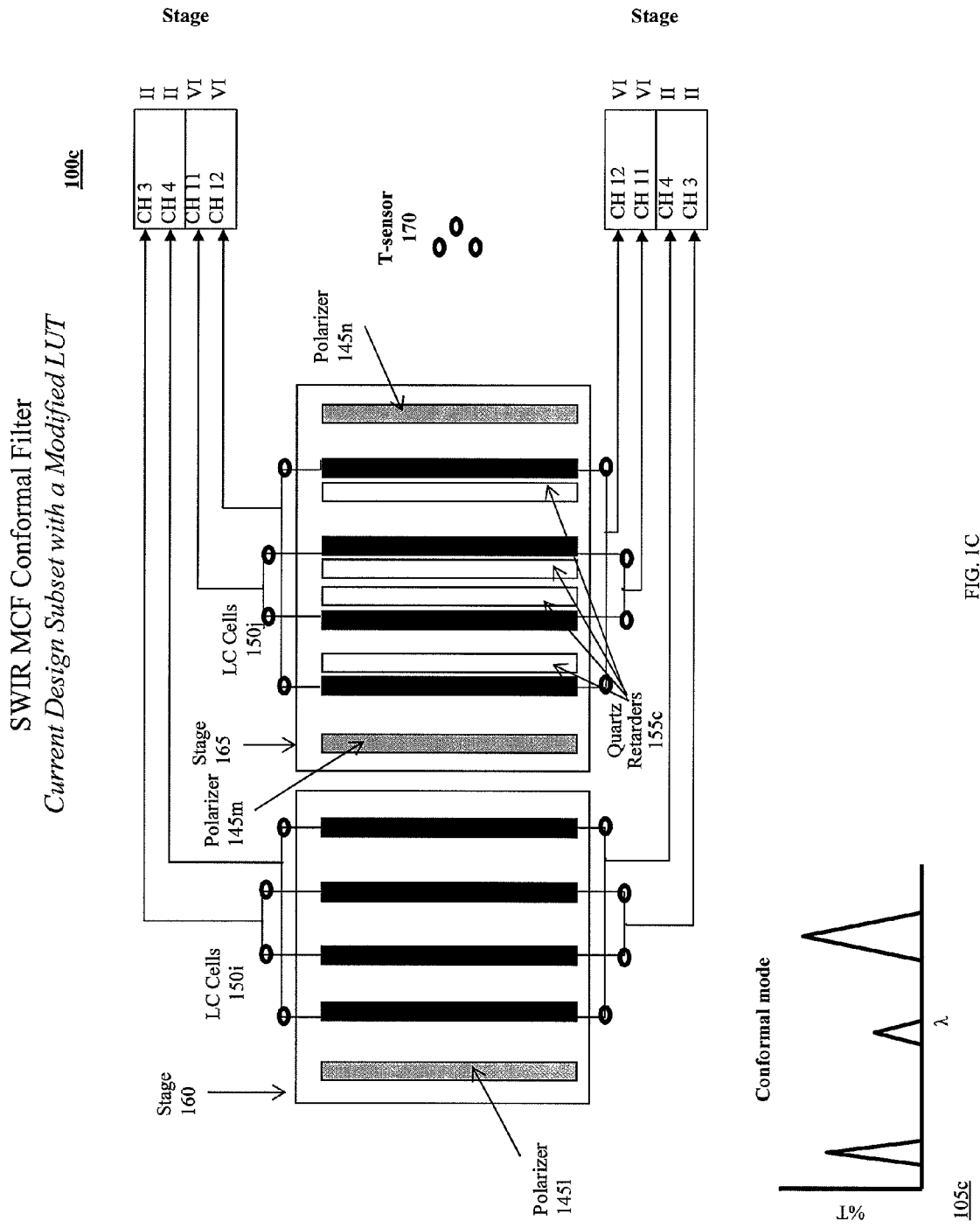

FIGS. 1A-1C illustrates conformal filter embodiments comprising a MCF which may operate in conjunction with one or more LUTs (not illustrated). In FIG. 1A, a hot mirror 135 may be operatively coupled to the MCF. A plurality of filter stages, 115, 120, 125, and 130 may be arranged in a Solc configuration. Each stage may comprise a combination of polarizers 145a-145d, liquid crystal (LC) cells 150a-150d, and quartz retarders 155a-155b. A first antireflective (AR) glass component 140a may be placed in front of the first polarizer 145a and a second AR glass component 140b may be placed after the last polarizer 145e. The filter may be operatively coupled to a temperature sensor 170 for monitoring the temperature of the filter and modifying the LUT as needed for temperature adjustments. Predicted transmission of the filter operating in both a bandpass and a conformal mode is also provided 110.

In FIG. 1B, the MCF 100b may comprise a polarizer 145f operatively coupled to the hot mirror 135 at an input of the MCF. The polarizer may be mounted to a rotatable aperture for increasing optical throughput. In one embodiment, the polarizer 145f may be at least one of the following: a mechanically rotatable polarizer and an electronically tunable LC cell. The polarizer 145f may be tuned as needed each time the MCF is tuned to a new configuration. Filter stages 115, 120, 125, and 130 may further comprise a combination of polarizers 145h-145k and liquid crystal (LC) cells 150e-150h. A first antireflective (AR) glass component 140c may be placed in front of polarizer 145g and a second AR glass component 140d may be placed after the last polarizer 145k. Predicted transmission of the MCF operating in conformal mode is also provided 105b.

In another embodiment, the present disclosure provides for a conformal filter comprising a modified MCF. In such an embodiment, a tunable filter may be modified or specifically designed so that selected individual stages of a traditional tunable filter comprise multiple, lower resolution liquid crystal cells. As illustrated by FIG. 1C, a MCF may be redesigned with fewer stages 160 and 165 for use as a conformal filter 100c. Selected filter stages 160 and 165 may comprise a combination of optical elements including polarizers 145l-145n, LC cells 150l-150j, and quartz retarders 155c. Predicted transmission of the conformal filter is also provided 105c.

The present disclosure contemplates that other configurations may be used to modify the MCF and that the present disclosure is not intended to be limited to the design in FIG. 1C. Other conformal filter designs may be selected using a robust, iterative, non-linear optimization methodology. Such a methodology may begin with a random starting configuration and be reconfigured until a minimum response is achieved. The present disclosure contemplates that any iterative, non-linear optimization method known in the art may be applied to design the conformal filter.

Figure 2A:
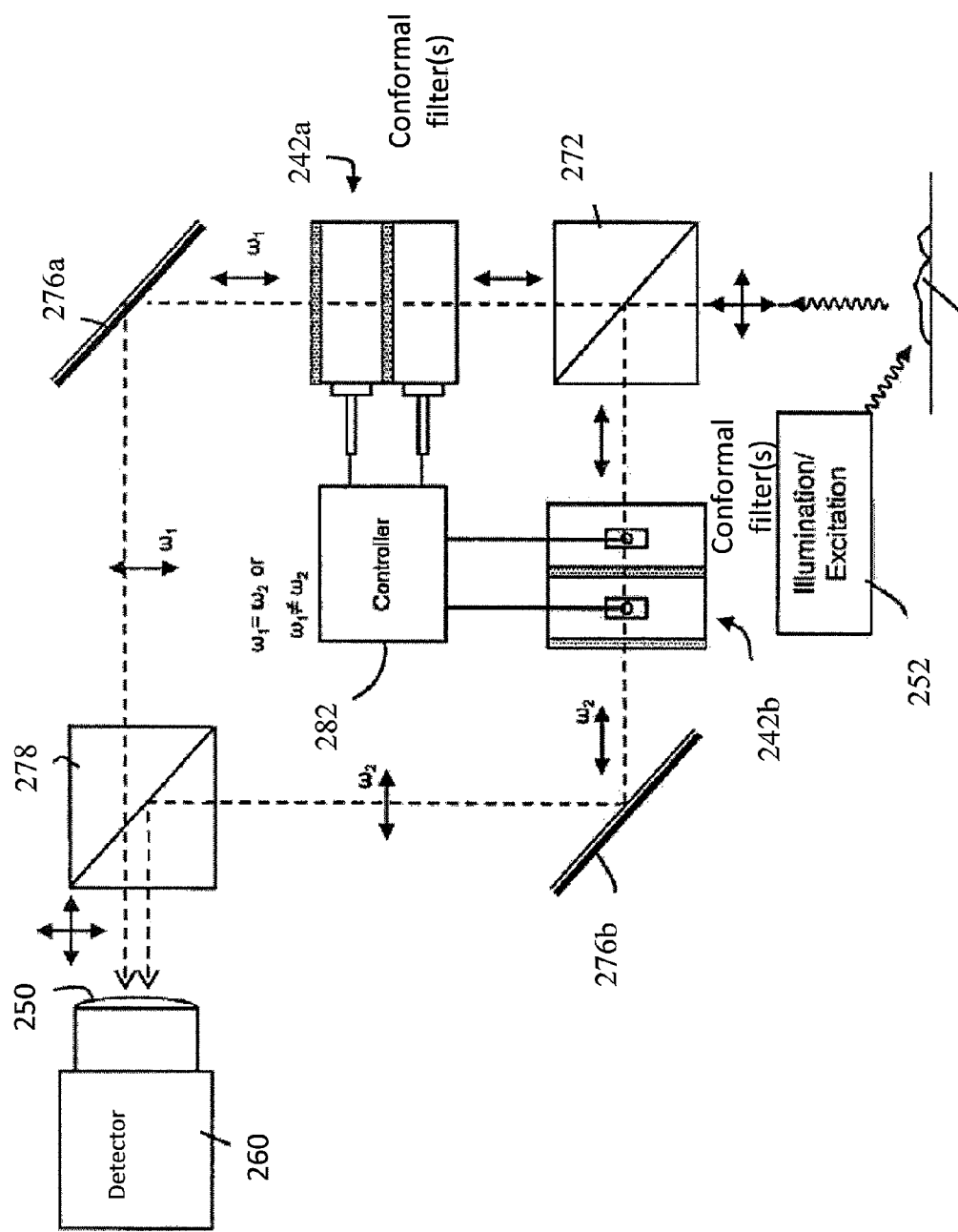
FIG. 2A is illustrative of a dual polarization configuration of the present disclosure comprising one detector.
Figure 2B:
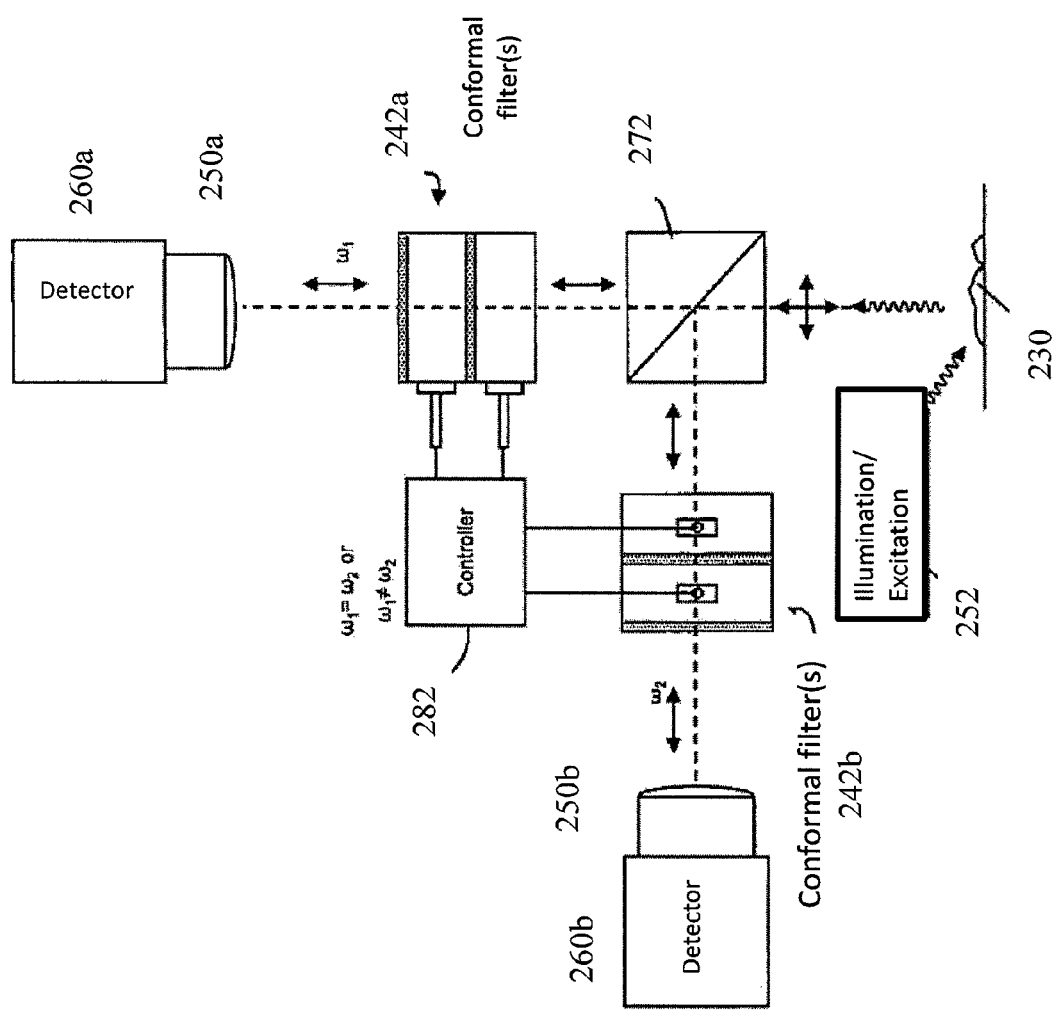
FIG. 2B is illustrative of a dual polarization configuration of the present disclosure comprising a plurality of detectors.
Figure 2C:
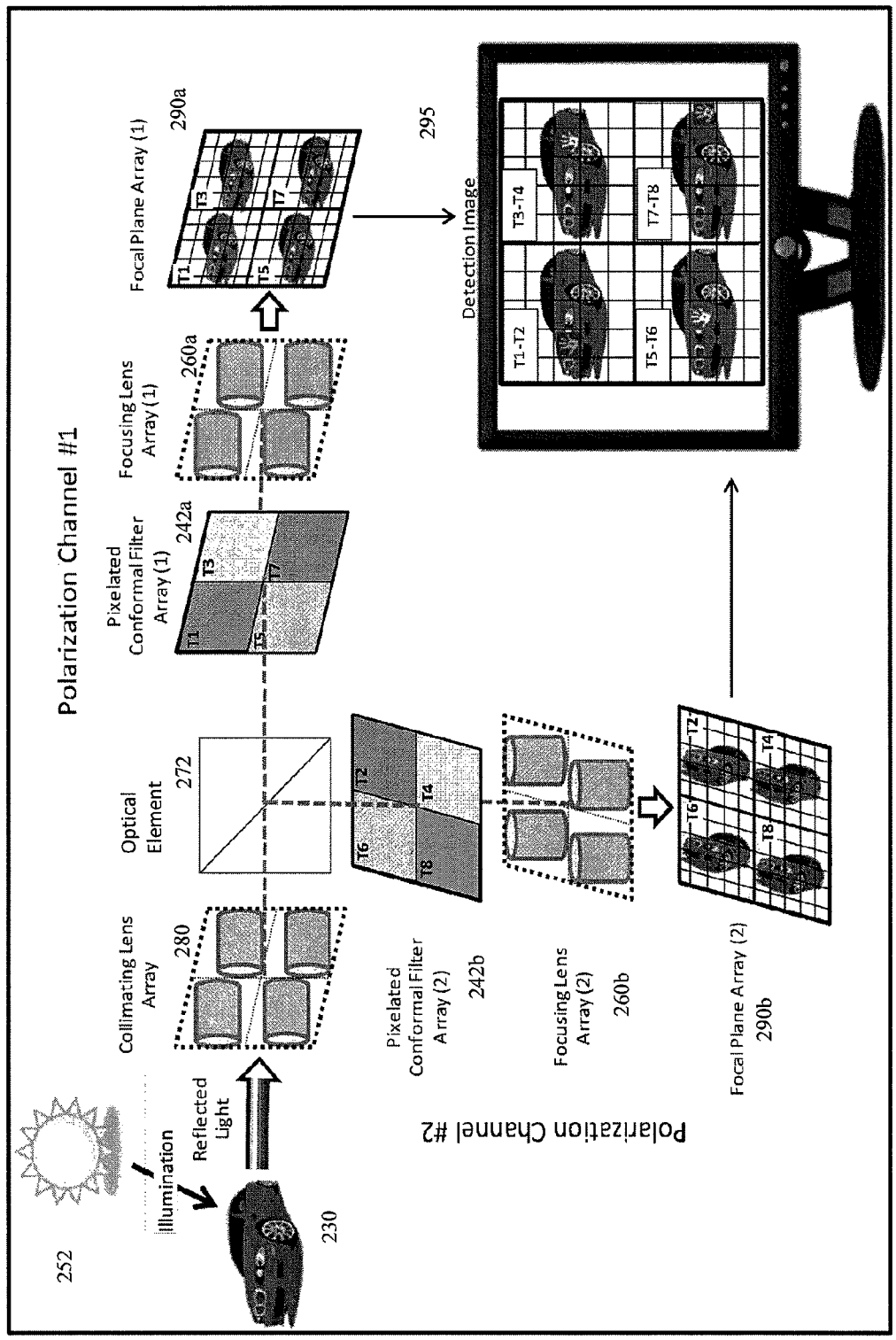
FIG. 2C is illustrative of a pixilated approach comprising a plurality of conformal filter assemblies.

The present disclosure also provides for a system comprising two or more conformal filters in a dual polarization configuration, exemplary configurations of which are illustrated in FIGS. 2A-2C. A preferred embodiment comprising a single detector is illustrated in FIG. 2A. Referring now to FIG. 2A, the sample 230 may be illuminated and/or excited by an illumination source 225. In one embodiment, the illumination source 225 may comprise an active illumination source, such as a laser. In another embodiment, the illumination source may comprise a passive illumination source such as solar radiation. Other examples of illumination sources may comprise: a quartz tungsten halogen lamp, a high-pressure mercury arc lamp, a light emitting diode, and a blackbody emitter. In one embodiment, it is possible to illuminate the sample from a laser directly in an oblique direction.

The embodiment of FIG. 2A comprises two independently tunable conformal filters 242a, 242b along distinct orthogonal beam paths for the orthogonal polarization components emerging from optical element 272. The present disclosure contemplates that optical element 272 may further comprise at least one of: a beamsplitter, a dichroic mirror, and an optical mirror. The beamsplitter may further comprise a polarizing beamsplitter or a non-polarizing beamsplitter.

In this arrangement, the paths of the filtered beams are not parallel through the conformal filters 242a, 242b, but are directed by appropriate reflectors (e.g., mirrors) 276a, 276b to a second optical element 278 (which may be a beam combiner, a polarizing cube or polarizing beam splitter as illustrated) at which the orthogonal components, which can be at the same or different spectral shapes $\omega 1$ and $\omega 2$. In one embodiment, the components may be combined and directed to a detector 260 through a lens assembly 250. In another embodiment, the components may be kept separate as they are directed to the detector 260. However, the beam paths from one optical element 272 to the other 278 (via individual conformal filters 242a, 242b) may be made symmetrical to avoid, for example, the need for infinitely-corrected optics.

In FIG. 2A, the detector 260 may comprise other detectors including but not limited to, at least one of: a CCD detector, a CMOS detector, an InGaAs detector, a platinum silicide (PtSi) detector, indium antimonide (InSb) detector, and a mercury cadmium telluride (HgCdTe) detector.

In FIG. 2A, the two conformal filters 242a, 242b may be tuned in unison to the same spectral shape ($\omega 1 = \omega 2$) using a controller 282. It is possible to configure the controller 282 to independently tune the spectral shapes $\omega 1$ and $\omega 2$ of the conformal filters 242a, 242b that respectively process orthogonal components of the input. Therefore, by appropriate control, the conformal filters can be tuned to the same spectral shape or to two spectral shapes ($\omega 1 \neq \omega 2$) at the same time. It is also possible for one conformal filter to be tuned to generate the positive regression vector of a spectral shape and a second conformal filter to be tuned to generate the negative regression vector of the spectral shape. The controller 282 may be programmable or implemented in software to allow a user to selectively tune each conformal filters 242a, 242b as desired.

In the embodiment of FIG. 2A, a fast switching mechanism (not shown) may be provided to switch between the two views (or spectral images) corresponding to spectral data collected by the detector 260 from each of the conformal filters 242a, 242b. Alternatively, such two spectral views or images (from two separate conformal filters) may be combined or overlaid into a single image, for example, to increase contrast or intensity or for comparison purposes. The embodiment in FIG. 2A is shown to include a single CCD detector 260 to capture the filtered signals received from the conformal filters 242a, 242b. In another embodiment, the second optical element 278 may be removed and two detector cameras may be used. An exemplary embodiment of such a configuration is illustrated in FIG. 2B. Each detector 260a and 260b may be optically coupled to a corresponding one of the two conformal filters 242a, 242b to capture filtered signals from the conformal filters and to responsively generate electronic signals that enable display of spectral images of the illuminated sample 230. The present disclosure contemplates that any number of conformal filters and associated detectors may be used to achieve the benefit of dual polarization as described herein.

In one embodiment, the two filtered signals may be detected simultaneously. As discussed herein, simultaneous detection of two different spectral shapes holds potential for real-time detection when displayed in a non-overlapping configuration (side-by-side, top to bottom, etc.). In another embodiment, the two filtered signals may be detected sequentially.

It is noted here that although laser light may be coherent, the light received from the sample 230 (e.g., light emitted, scattered, absorbed, and/or reflected) and fed to the conformal filters 242a, 242b may not be coherent. Therefore, wavefront errors may not be present or may be substantially avoided in the two conformal filters versions in FIGS. 2A and 2B because of processing of non-coherent light by each conformal filters 242a, 422b.

The present disclosure also provides for a system comprising a PCF configuration. A PCF approach extends the idea of a traditional conformal filter approach, essentially creating an "array" of conformal filters, with each "pixel" in the array corresponding to a particular confirmation. This means that each pixel in the filter has a separately encoded, multivariate spectral pattern, specific to a given analyte. A PCF approach allows for the detection of multiple analytes simultaneously, where two conformal filters are needed for assessing each analyte (one corresponding to a positive regression vector and one corresponding to a negative regression vector). Using a dual polarization configuration, as described in reference to FIGS. 2A and 2B, at least two data collections may be captured simultaneously. In addition to increasing detection speed for both stationary and on-the-move (OTM) implementations, such a configuration holds potential for reducing motion induced artifacts and potential false positives due to slight changes in a scene between data collections while OTM. Alignment techniques, along with stereo vision and jitter suppression techniques may also be applied to compensate for motion detection.

One embodiment is illustrated by FIG. 2C. Here, interacted photons from a sample 230 are passed through at least one lens 280 to orient the photons in collimated space. The photons may be passed through an optical element 272 to separate the photons into at least a first optical component and a second optical component. The first optical component may be passed through a plurality of conformal filters, represented in FIG. 2C as a pixilated conformal filter array. The filtered optical components may be passed through a lens 290a and 290b to focus the each optical component onto a detector. In FIG. 2C, the detectors are illustrated as FPAs 260a and 260b. In one embodiment, a processor (not illustrated) may utilize software to recombine the data sets. This may be achieved my applying at least one optical computation to the first and second data sets. A detection image, a result of the application of the optical computation, may be displayed on a monitor or other device 295. The detection image is representative of the characteristic of the analyte under analysis. As illustrated in FIG. 2C, a PCF approach enables multiple analytes to be analyzed simultaneously.

The embodiment in FIG. 2C illustrates a four-pixel PCF configuration. Here, each pixel in the PCF corresponds to one of two confirmations required for the assessment of each of four anlaytes. Information associated with confirmation 1 for each of four analytes (T1, T3, T5, and T7) is captured on a first FPA 290a. Information associated with conformation 2 for each of the four analytes (T2, T4, T6, and T8) is captured on a second FPA 290b. The embodiment of FIG. 2C applies wavelength subtraction to achieve the detection image. However as discussed above the present disclosure contemplates other optical computations known in the art may also be applied.

The present disclosure contemplates a conformal filter may be incorporated into one or more HSI systems using either the dual polarization or PCF configurations described herein. Examples of HSI modalities which may incorporate the system and method described herein may include, but are not limited to: Raman, UV, fluorescence, VIS, and infrared (including SWIR, MWIR, and LWIR). In one embodiment, at least one HSI modality may be used to scan an area to identify regions of interest for further interrogation using one or more conformal filters.

The present disclosure also provides for a method for assessing characteristics of analytes. In one embodiment, illustrated by FIG. 3, the method may comprise collecting a plurality of interacted photons from a sample in step 310. The plurality of interacted photons may comprise at least one of: photons reflected by the sample, photons absorbed by the sample, photons scattered by the sample, and photons emitted by the sample. The plurality of interacted photons may be generated by illuminating at least a portion of a sample. The present disclosure contemplates that at least one of active illumination and passive illumination may be used.

In step 320 the plurality of interacted photons may be separated into a least a first optical component and a second optical component. In one embodiment, one or more lenses may be used to orient the plurality of interacted photons into culminated space. The first optical component may be passed through at least one conformal filter in step 330 and a second optical component may be passed through at least one conformal filter in step 340. Each conformal filter may comprise a tunable filter configured to filter an optical component conforming to at least one spectral shape associated with a target of interest. In one embodiment, a first conformal filter may be configured to generate a positive regression vector associated with the spectral shape, while a second conformal filter may be configured to generate a negative regression vector associated with the spectral shape.

In step 350 a first data set may be generated corresponding to the first filtered optical component. In step 360 a second data set may be generated corresponding to the second filtered optical component. In one embodiment, at least one of the first and second data sets may further comprise at least one of: a spectral intensity of the sample and a spectral image representative of the sample. In one embodiment, the first test data set and the second test data set may be generated by the same detector. In another embodiment, the first data set and the second data set may be generated by two different detectors. The present disclosure contemplates embodiments where detecting the first and second data set may be simultaneous or sequential and the data sets may be displayed in an overlaid configuration or a configuration other than overlaid.

At least one optical computation may be applied in step 370 to the first and second data set to assess the sample for at least one characteristic of the analyte. The optical computation may be any known in the art including, but not limited to: wavelength addition, wavelength subtraction, wavelength multiplication, and wavelength division and may also be referred to as a mathematical computation. The result of applying the optical computation may be a detection image, indicative of one or more characteristics of each analyte under analysis. Examples of characteristics that may be assessed may include, but are not limited to, at least one of: the presence of the analyte in the sample, the absence of the analyte in the sample, a classification of the analyte, a non-classification of the analyte, and a concentration of the analyte.

In one embodiment, the configuration of at least one conformal filter may be determined by searching at least one LUT corresponding to an analyte of interest, wherein the LUT comprises at least one voltage associated with each stage of the tunable filter, and wherein each voltage is configured to cause the tunable filter to conform to a spectral shape associated with the analyte of interest when applied to the associated stage.

The present disclosure also provides for a method for selecting a conformal filter configuration using an iterative process. This method is referred to herein as Real-time Contrast Enhancement (RtCE) and provides for configurations with high analyte specificity and sensitivity by applying active tunable filter voltage adjustment and feedback from a live measurement scene. Such an approach may be used to calibrate a conformal design for an analyte of interest, refine a previous conformal filter design for an analyte of interest, and/or generate a new conformal filter design for an analyte of interest.

Figure 4:
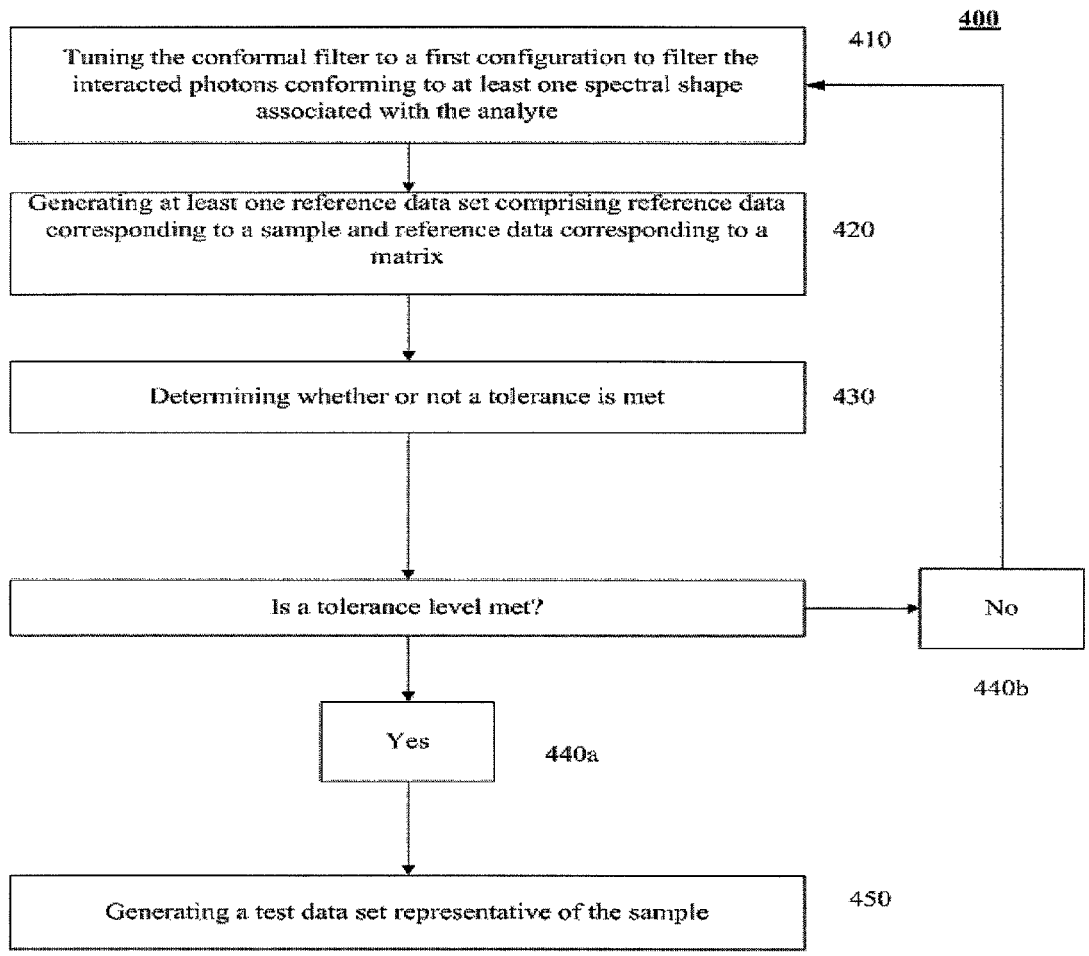
FIG. 4 is illustrative of a method of the present disclosure.

One embodiment of this optimization process is provided in FIG. 4. The method 400 may comprise tuning at least one conformal filter to a first configuration to filter interacted photons conforming to at least one spectral shape associated with an analyte in step 410. In step 420, at least one reference data set may be generated comprising reference data corresponding to a sample and reference data corresponding to a matrix. In one embodiment, the reference data set may comprise at least one reference spectrum associated with the sample and at least one reference spectrum associated with the matrix.

In another embodiment, at least one reference data set may comprise at least one reference image comprising the sample and the matrix. A first region of interest may be selected corresponding to the sample and a second region of interest may be selected corresponding to the matrix. Spectral data may be extracted from these regions of interest.

In one embodiment, at least one chemometric technique may be applied to the at least one reference data set (e.g. spectral data). Examples of chemometric techniques include, but are not limited to: correlation analysis, principle component analysis, principle component regression, partial least squares, multivariate curve resolution, Mahalanobis distance, Euclidian distance, band target entropy, band target energy minimization, partial least squares discriminant analysis, adaptive subspace detection, and combinations thereof. Chemometric techniques may be used to compare test data to reference data.

One or more optical computations may also be applied to the test data set. In addition to wavelength addition, wavelength subtraction, wavelength multiplication, and wavelength division, this optical computation may comprise at least one of the following: T1, and (T1−T2)/(T1+T2), among others known in the art.

A determination of whether or not a tolerance level is met may be made in step 430. In one embodiment, this determination may comprise applying at least one Figure of Merit (FOM) A FOM is a numerical value that may be used to guide the optimization process. Examples of figures of merit that may be applied include, but are not limited to: Standard error of calibration (SEC), Euclidian Distance, standard error of prediction (SEP), 1-Area Under the Receiver Operator Characteristic Curve (AUROC), optical throughput (% T), and combinations thereof. Other FOMs may be used that incorporate optical throughput, signal to noise ratio (SNR), among others. If a tolerance level is met 440a, then a test data set representative of the sample may be generated in step 450. If a tolerance level is not met 440b, then the process may be repeated for at least one other conformal filter configuration until a tolerance level is met. In one embodiment, the present disclosure contemplates the method of FIG. 4 may be utilized to tune each conformal filter in a dual polarization or PCF configuration.

The present disclosure also provides for a system comprising a processor and a non-transitory processor-readable storage medium in operable communication with the processor, wherein the storage medium may contain one or more programming instructions that, when executed, cause the processor to perform the following: collect a plurality of interacted photons from a sample, separate the plurality of interacted photons into at least a first optical component and a second optical component, pass the first optical component through at least one conformal filter, pass the second optical component through at least one conformal filter, generate a first data set associated with the first filtered optical component and a second data set associated with a second filtered optical component, and apply at least one optical computation to the first data set and the second data set to assess the sample for at least one characteristic of the analyte. The storage medium may further contain programming instructions that cause the processor to select conformal filter configurations by searching a LUT corresponding to an analyte and applying the configuration to the conformal filter.

In another embodiment, the system may further comprise one or more programming instructions that, when executed, cause the processor to iteratively configure the conformal filter until a tolerance level is met. In such an embodiment, the instructions may cause the processor to tune the conformal filter to a first configuration to filter interacted photons conforming to at least one spectral shape associated with the analyte, generate at least one reference data set comprising reference data corresponding to the sample and reference data corresponding to a matrix, and determine whether or not a tolerance level is met. If a tolerance level is met, a test data set may be generated. If a tolerance level is not met, then the steps may be repeated for one or more difference configurations until a tolerance level is met. In one embodiment, whether or not a tolerance level is met may be determined by the processor applying at least one figure of merit. In other embodiments the processor may further analyze the test data set by applying at least one of the following: an optical computation and a chemometric technique.

Examples

Figure 5A:
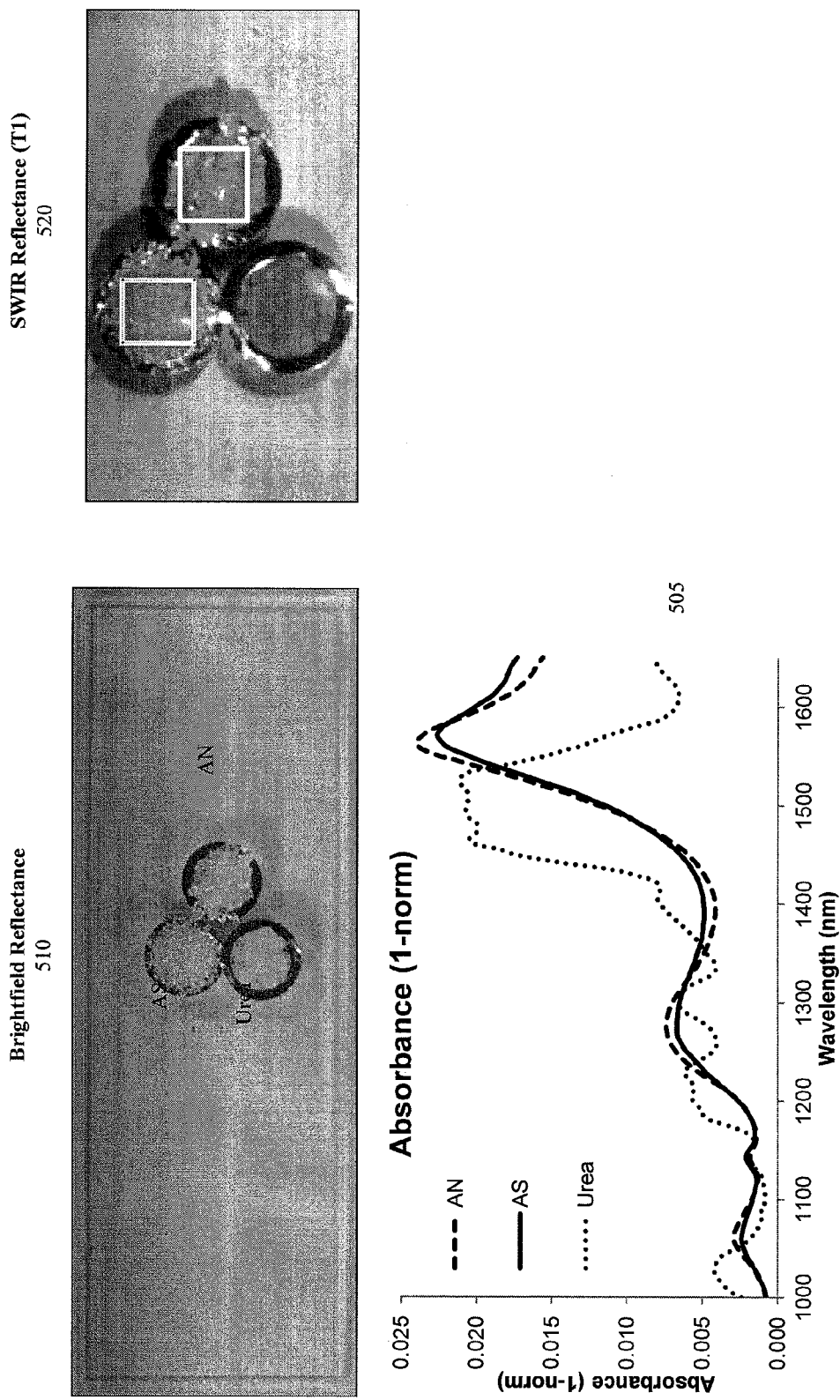
FIGS. 5A-5C are illustrative of the detection capabilities of a system and method of a conformal filter.
Figure 5B:
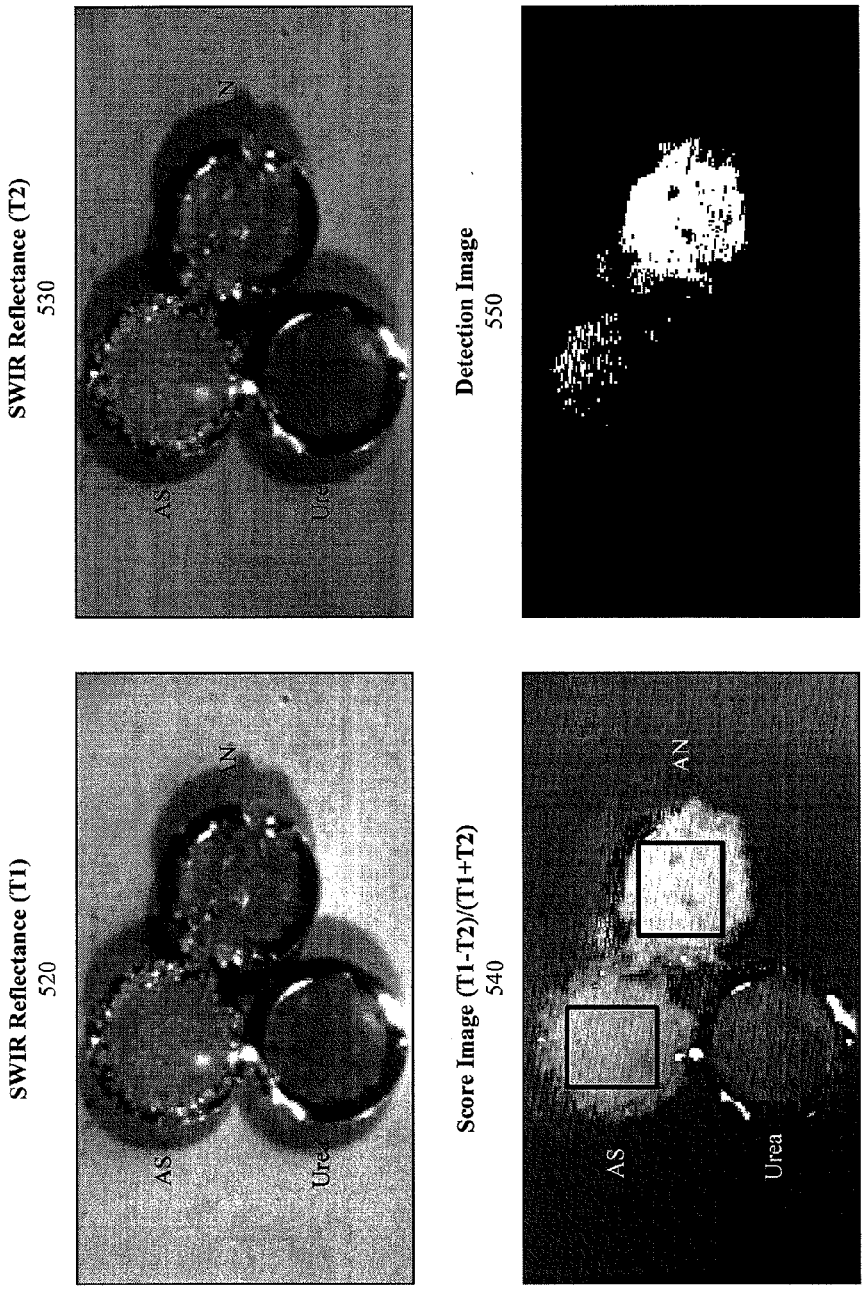
Figure 5C:
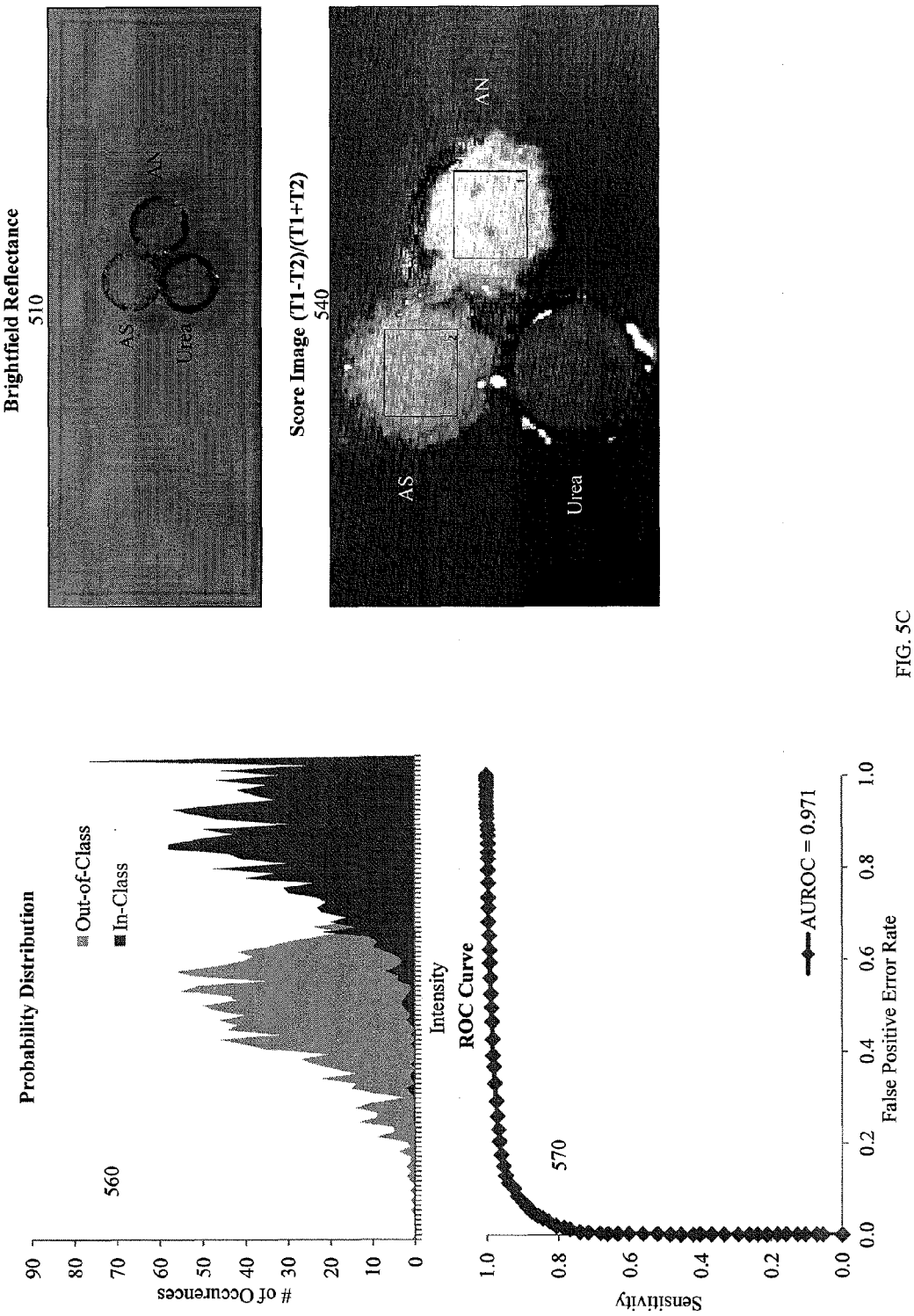

FIGS. 5A-5C are illustrative of the detection capabilities of a conformal filter of the present disclosure. While this data was generated using one conformal filter and not dual polarization or PCF configurations, it is illustrative of the detection potential of a system and method of the present disclosure. Use of dual polarization and PCF configurations would enable increased speed of detection and the assessment of multiple anlaytes simultaneously.

Three samples were prepared comprising AS, AN, and urea. AN was selected as the analyte of interest, AS was selected as a confusant (background), and urea was selected as an interferent. The samples were analyzed using an experimental set up wherein the illumination source comprised a quartz tungsten halogen lamp, the conformal filter comprised a MCF, and the detector comprised a SWIR camera. A brightfield reflectance image 510 and a SWIR reflectance image (T1) 530 were generated. Spectral data for each substance 505 is also illustrated in FIG. 5A, FIG. 5B illustrates the detection capabilities of the present disclosure when an RtCE methodology is applied. A second SWIR reflectance image (T2) was generated 530. The optical computation (T1−T2)/(T1+T2) was applied, and a score image 540 was generated. As can be seen from the detection image 550, AN was easily detected and distinguished from AS and urea. FIG. 5C is illustrative of the detection results after applying additional processing steps such as contrast flip and saturation removal. A probability distribution 560, from the score image 540, illustrates in-class v. out-of-class detections. The ROC curve 570 illustrates the sensitivity and false positive results achieved and was generated by applying a threshold to the probability distribution 560. As illustrated by the Examples, the system and method of the present disclosure enables analyte detection and "near neighbor" discrimination (i.e., analytes with similar spectral features.)

While the disclosure has been described in detail in reference to specific embodiments thereof, it will be apparent to one skilled in the art that various changes and modifications can be made therein without departing from the spirit and scope of the embodiments. Additionally, while the examples provided herein relate to specific analytes, the present disclosure is not limited to these analytes and may be used to detect a wide variety of analytes of interest. Thus, it is intended that the present disclosure cover the modifications and variations of this disclosure provided they come within the scope of the appended claims and their equivalents.

What is claimed is:

1. A method comprising:
    collecting a plurality of interacted photons from a sample;
    separating the plurality of interacted photons into at least a first optical component and a second optical component;
    passing the first optical component and the second optical component through at least one conformal filter comprising a tunable filter having one or more filter stages and configured to filter one or more of the first optical component and the second optical component to conform to at least one spectral shape associated with an analyte of interest, wherein the configuration of the tunable filter is determined by searching at least one look-up table comprising at least one voltage associated with each stage of the tunable filter where each voltage is configured to cause the tunable filter to conform to a spectral shape associated with the analyte of interest when applied to a corresponding stage;
    generating a first data set corresponding to the first filtered optical component;
    generating a second data set corresponding to the second filtered optical component; and
    applying at least one optical computation to the first data set and the second data set to assess the sample for at least one characteristic of the analyte.

2. The method of claim 1 wherein the characteristic comprises at least one of: the presence of the analyte in the sample, the absence of an analyte in the sample, a classification of the analyte, a non-classification of the analyte, and a concentration of the analyte.

3. The method of claim 1 wherein the first data set comprises at least one of: a spectral intensity of the sample and a spectral image representative of the sample.

4. The method of claim 1 wherein the second data set comprises at least one of: a spectral intensity of the sample and a spectral image representative of the sample.

5. The method of claim 1 wherein the first data set is generated by a first detector and the second data set is generated by a second detector.

6. The method of claim 1 wherein the first data set and the second data set are generated by the same detector.

7. The method of claim 6 wherein the first data set and the second data set are displayed in an overlaid configuration.

8. The method of claim 6 wherein the first data set and the second data set are displayed in a configuration other than overlaid.

9. The method of claim 1 wherein the first data set and the second data set are generated simultaneously.

10. The method of claim 1 wherein the first data set and the second data set are generated sequentially.

11. The method of claim 1 wherein the optical computation comprises at least one of: wavelength subtraction, wavelength addition, wavelength division, and wavelength multiplication.

12. The method of claim 1 wherein the interacted photons comprise at least one of: photons absorbed by the sample, photons reflected by the sample, photons emitted by the sample, and photons scattered by the sample.

13. The method of claim 1 wherein the interacted photons are generated by illuminating at least a portion of the sample using at least one of: active illumination and passive illumination.

14. The method of claim 1 further comprising passing the plurality of interacted photons through at least one lens to thereby orient the plurality of interacted photons in collimated space.

15. The method of claim 1 further comprising passing the first optical component and the second optical component through a plurality of conformal filters, each conformal filter configured to filter each optical component conforming to at least one spectral shape associated with at least one other analyte of interest.

16. A system comprising:
    a first optical element configured to separate a plurality of interacted photons generated from a sample into at least a first optical component and a second optical component;
    at least one conformal filter assembly configured to filter the first optical component and second optical component to conform to a least one spectral shape associated with an analyte of interest, and each conformal filter assembly further comprises:
        a first conformal filter comprising a first tunable filter having one or more filter stages and configured to filter the first optical component conforming to a positive regression vector associated with the spectral shape associated with the analyte of interest, and
        a second conformal filter comprising a second tunable filter having one or more filter stages and configured to filter the second optical component conforming to a negative regression vector associated with the spectral shape associated with the analyte of interest;
    a look-up table comprising at least one voltage associated with each filter stage of the first tunable filter and the second tunable filter, where the at least one voltage is configured to cause the first tunable filter and the second tunable filter to conform to a spectral shape associated with the analyte when the at least one voltage is applied to the associated filter stage; and
    at least one detector configured to detect at least one of the first filtered optical component and the second filtered optical component and generate at least one of: a first data set associated with the first filtered optical component and a second data set associated with the second filtered optical component.

17. The system of claim 16 wherein the first optical element further comprises at least one of: an optical mirror, a dichroic mirror, and a beamsplitter.

18. The system of claim 17 wherein the beamsplitter further comprises at least one of: a polarizing beamsplitter and a non-polarizing beamsplitter.

19. The system of claim 16 further comprising at least one lens configured to orient the plurality of interacted photons into collimated space for delivery to the first optical element.

20. The system of claim 16 wherein a first detector detects the first filtered optical component and generates the first data set, and a second detector detects the second filtered optical component and generates the second data set.

21. The system of claim 16 wherein one or more of the first conformal filter and the second conformal filter is configured to enable tuning to a plurality of configurations, wherein each configuration is designed to filter interacted photons conforming to at least one spectral shape associated with at least one analyte.

22. The system of claim 16 wherein one or more of the first tunable filter and the second tunable filter comprises at least one of: a liquid crystal tunable filter, a multi-conjugate tunable filter, an acousto optical tunable filter, a Lyot liquid crystal tunable filter, an Evans Split-Element liquid crystal tunable filter, a Solc liquid crystal tunable filter, Fabry Perot liquid crystal tunable filter, and a Ferroelectric liquid crystal tunable filter.

23. The system of claim 16 further comprising at least one illumination source configured to illuminate the sample and generate the plurality of interacted photons.

24. The system of claim 23 wherein the illumination source comprises a broadband light source.

25. The system of claim 24, wherein the broadband light source comprises at least one of the following: a quartz tungsten halogen lamp, a high-pressure mercury arc lamp, solar radiation, a light emitting diode, and a blackbody emitter.

26. The system of claim 16 wherein at least one of the first detector and the second detector comprises at least one of: an InGaAs detector, a CCD detector, a CMOS detector, an InSb detector, and a MCT detector.

27. The system of claim 16 further comprising a processor configured to analyze at least one of the first data set and the second data set to assess the sample for at least one characteristic of the analyte.

28. The system of claim 27 wherein the characteristic comprises at least one of: the presence of the analyte in the sample, the absence of an analyte in the sample, a classification of the analyte, a non-classification of the analyte, and a concentration of the analyte.

29. The system of claim 16 further comprising configuring the first detector to display the first data set and the second data set in an overlaid configuration.

30. The system of claim 16 further comprising configuring the first detector to display the first data set and the second data set in a configuration other than overlaid.

31. The system of claim 16 further comprising a second beamsplitter configured to recombine the first filtered optical component and the second filtered optical component.

32. The system of claim 16 further comprising at least one lens configured to focus the first filtered optical component and the second filtered optical component onto at least one detector.

33. The system of claim 16 further comprising a plurality of conformal filter assemblies wherein each conformal filter assembly is configured to filter the first optical component and second optical component conforming to a least one spectral shape associated with at least one other analyte of interest.

34. A system comprising:
a processor; and
a non-transitory processor-readable storage medium in operable communication with the processor, wherein the storage medium contains one or more programming instructions that, when executed, cause the processor to perform the following:
collect a plurality of interacted photons from a sample,
separate the plurality of interacted photons into at least a first optical component and a second optical component,
pass the first optical component and the second optical component through at least one conformal filter comprising a tunable filter having one or more filter stages and configured to filter an optical component conforming to at least one spectral shape associated with an analyte of interest,
cause at least one voltage to be applied to each filter stage of the tunable filter by accessing a look-up table corresponding to an analyte of interest, wherein each voltage causes the tunable filter to conform to a spectral shape associated with the analyte when applied to the associated stage;
generate a first data set corresponding to the first filtered optical component,
generate a second data set corresponding to the second filtered optical component, and
apply at least one optical computation to the first data set and the second data set to assess the sample for at least one characteristic of the analyte.

* * * * *